United States Patent [19]

Msika et al.

[11] Patent Number: 6,146,616
[45] Date of Patent: Nov. 14, 2000

[54] ANTIOXIDANT AND/OR ANTIELASTASE COMPOSITION BASED ON LUPINE OIL

[75] Inventors: Philippe Msika, Paris; Alain Rancurel, Leves; Marie-Georgette Montaudoin, Maintenon, all of France

[73] Assignee: Laboratories Pharmascience, Courbevioe, France

[21] Appl. No.: 09/202,959

[22] PCT Filed: Apr. 24, 1998

[86] PCT No.: PCT/FR98/00827

§ 371 Date: Dec. 24, 1998

§ 102(e) Date: Dec. 24, 1998

[87] PCT Pub. No.: WO98/47479

PCT Pub. Date: Oct. 29, 1998

[30] Foreign Application Priority Data

Apr. 24, 1997 [FR] France .................................. 97 05067

[51] Int. Cl.⁷ ................................ A61K 7/42; A61K 7/00
[52] U.S. Cl. ............................ 424/59; 424/400; 424/401
[58] Field of Search ..................................... 424/400, 401, 424/59

[56] References Cited

FOREIGN PATENT DOCUMENTS

| | | |
|---|---|---|
| 0 302 769 | 2/1989 | European Pat. Off. . |
| 0 441 672 | 8/1991 | European Pat. Off. . |
| 2 692 783 | 12/1993 | France . |
| 21 55 727 | 5/1973 | Germany . |
| 33 29 249 | 2/1985 | Germany . |

OTHER PUBLICATIONS

"Use of Lupine as a Protein–Oil Food Source," Fichier Chemical Abstracts, vol. 102, AN 77429, XP–002052109 (1983).

"Lupine Oil—Its Use as Food," Fichier Chemical Abstracts, vol. 101, AN 150094, XP–002052110, (1984).

*Primary Examiner*—Shelley A. Dodson
*Attorney, Agent, or Firm*—Foley & Lardner

[57] ABSTRACT

The invention concerns an antioxidant and/or antielastase composition containing lupine oil or one or several fractions thereof, its use in cosmetics, pharmaceutics and as food additive. More particularly it concerns a composition containing a mixture of lupine oil and wheat germ concentrate, preferably in a proportion of 70 wt. % of lupine oil and 38 wt. % of wheat germ concentrate.

29 Claims, No Drawings

ANTIOXIDANT AND/OR ANTIELASTASE COMPOSITION BASED ON LUPINE OIL

The subject of the present invention is new compositions based on lupine oil, or on fractions thereof, especially concentrates and unsaponifiable matter.

Lupine oil may be extracted especially from lupine meals and/or seeds.

Lupine is a close relative of the pea, broad bean, soybean and French bean. The seed is traditionally used as human food for its high protein content. It is also incorporated into ruminant feed in the form of a whole plant or of its seeds and is also frequently used as green manure. More particularly, four species of lupine are of real agronomic importance: white lupine (*lupinus albus*), blue lupine (*lupinus angustifolius*), yellow lupine (*lupinus luteus*) and South American lupine (*lupinus mutabilis*).

Plants constitute an abundant lipid source and the extraction of vegetable oil has already been widely carried out. The oil can then be used directly, or in the form of some of its fractions. Among the fractions which can be obtained from a vegetable oil, there may be mentioned the unsaponifiable matter or the concentrates.

According to the European Pharmacopeia, 2nd edition, page V.3.4.7, the term "unsaponifiable" applies to the non-volatile substances obtained by extraction, with an organic solvent, of a solution of the substance to be examined after saponification of a vegetable or animal oil.

Moreover, the so-called molecular distillation method makes it possible to concentrate oils derived in particular from plants (vegetable oils), and to obtain concentrates in which the concentration of unsaponifiable matter may reach, for example, the order of 10% to 20% by weight, or even greater, this concentration being of the order of 1% to 2% by weight in the original oils.

Vegetable oils have thus been the subject of various uses, mainly in cosmetology. For example, Patent FR 92 07830 describes the preparation of compositions based on unsaponifiable fractions of wheatgerm and sesame oils for a cosmetic use, these concentrates being obtained by molecular distillation according to a preferred method described in the patent.

As regards lupine oil, no cosmetic or pharmaceutical use has been envisaged up to date. European Patent Publication EP-A-441672 describes a process for the extraction of constituents of a plant material which make it possible in particular to obtain a lupine oil without any trace of alkaloid. This document describes in particular the treatment of the bitter lupine seeds and aims essentially to enhance the value of a protein cake free of the bitterness characteristic of bitter lupine seeds.

The inventors have now observed that, surprisingly, a composition containing lupine oil or one or more fractions thereof had a number of properties paving the way to a variety of applications in the cosmetic, pharmaceutical or food domain.

The studies on which the invention is based have made it possible to demonstrate that lupine oil or its fractions exert especially an antioxidant and antielastase activity.

The subject of the present invention is therefore an antioxidant and/or antielastase composition containing lupine oil or one or more fractions thereof. The lupine oil may be extracted from lupine meals and/or seeds.

The lupine oil may be obtained by any known method, in particular by direct pressing of the lupine seeds.

So-called sweet lupine species, that is to say free of bitterness, will be preferably used as raw material for the production of the lupine oil or of its fractions. There may be mentioned especially white lupine, blue lupine, yellow lupine and South American lupine, in particular white lupine (*lupinus albus*). The lupine oil extracted from this lupine variety is then free of undesirable alkaloids.

The invention relates more particularly to a composition comprising lupine oil in the form of a fraction consisting of a lupine oil concentrate obtained by molecular distillation of said oil.

According to a preferred embodiment, the compositions based on lupine oil according to the invention comprise one or more lupine oil fractions in the form of unsaponifiable matter as contained in a lupine oil concentrate obtained by molecular distillation of said oil.

Advantageously, the quantity by weight of the unsaponifiable fraction in the lupine oil concentrate is about 30% to about 70%, preferably about 45% to about 65% and still more preferably of the order of 60%.

The inventors have observed that lupine oil has a particularly high content of polyphenol, β-carotene and tocopherol derivatives and it is known that the polyphenol derivatives contribute to the oxidation-stability of a composition containing them. Advantageously, the subject of the invention is an antioxidant and/or antielastase composition which contains a lupine oil fraction comprising phenol derivatives. More generally, the invention also relates to any antioxidant and/or antielastase composition which contains phenol derivatives extracted from lupine oil. Preferably, the content of phenol derivatives is equal to at least 20 ppm.

The subject of the invention is also a composition in which the lupine oil or its fractions are in the form of a mixture with wheatgerm oil or one or more of its fractions. In this case, the wheatgerm oil fraction used may also be a concentrate obtained by molecular distillation of said oil or alternatively an unsaponifiable fraction contained in such a concentrate. Surprisingly, the inventors have now established that wheatgerm oil or its fractions could be advantageously used in combination with lupine oil or its fractions.

Preferably, when the two types of oil are present in a composition according to the invention, the lupine oil is in the form of a mixture with a wheatgerm oil concentrate.

According to a preferred embodiment of the invention, the quantities by weight of concentrate of wheatgerm oil and of lupine oil vary respectively between about 10% and about 90% and between about 90% and about 10% so that the quantities of these two oils is 100% in total.

Surprisingly, it has moreover been observed that in a certain composition ratio, the antioxidant, in particular anti-free radical, activity was substantially better.

Accordingly, a preferred composition according to the invention is that in which the quantities by weight of the concentrate of wheatgerm oil and of lupine oil are respectively 30% and 70%.

The invention also relates to the cosmetic use of a composition according to the invention, especially as antioxidant, anti-free radical agent, antielastase agent, agent for protecting against UVA and/or B, agent for protecting DNA against damage, especially oxidative damage. By virtue of the activities demonstrated for the compositions according to the invention, it is possible to use the compositions according to the invention for cosmetic or pharmaceutical purposes, especially for photoprotection, against actinic aging or otherwise, and for protecting the skin against oxidative attacks including pollution.

The invention also relates to the compositions according to the invention as a pharmaceutical, especially dermatological, product and more particularly as an agent intended for the prevention or for the treatment of the effects of UVA and/or UVB radiation on the skin, at the epidermal, dermal, cellular or extracellular levels, as a pharmaceutical product for the prevention and treatment of the effects of oxidation, of elastase and of free radicals on the skin, or alternatively as an agent having an activity of protecting DNA against damage, especially oxidative damage.

The subject of the invention is also a method of cosmetic treatment comprising the application of an antioxidant or antielastase composition or of a cosmetic composition according to the invention on the skin surface of an individual.

Under another aspect, the invention relates to a cosmetic or pharmaceutical composition comprising a composition according to the invention, preferably in combination with a physiologically acceptable vehicle.

The cosmetic or pharmaceutical compositions thus defined are capable of being used in particular as an antisun product for protecting against UVB and/or A radiation and/or infrared radiation, a restructuring or toning cream, a product, especially a cream, for the prevention and the regression of vibices, a nutritive cream, antiwrinkle cream (for combating aging of the skin, epidermis and dermis) and protective day cream, contour of the lips and of the eyes, regenerative and protective lipsticks. For these uses, the cosmetic compositions according to the invention are advantageously formulated for a topical use, especially in the form of creams, emulsions, ointments, sticks or gels.

The cosmetic or pharmaceutical compositions according to the invention may have a total content by Weight of lupine oil or its fractions and wheatgerm oil or its fractions of the order of 0.5 to 10% approximately, preferably from about 1% to about 5%.

The antioxidant activity of the compositions according to the invention, demonstrated by the oxidation-stability especially of the lupine oil and of the corresponding concentrate, is particularly advantageous because it offers possibilities of additional uses as a dietary supplement taking advantage of this antioxidant activity.

Finally, the subject of the invention is also a process for preparing the compositions described above. Different variations may be envisaged depending on the compositions. Thus, for example, there may be mentioned:

the mixture of two concentrates of lupine oil and of wheatgerm oil as obtained by the molecular distillation method, for example, as described in the review "Parfumerie Cosmétique et Arôme" [Cosmetic Perfumery and Fragrance] (1985, No. 61, page 91–96);

the preliminary mixing of lupine and wheatgerm oils followed by molecular distillation of the mixture according to the process described above;

the mixture of lupine oil and of a wheatgerm oil concentrate obtained by molecular distillation.

The wheatgerm oil concentrate is advantageously prepared according to the molecular distillation process described in Patent FR 92 07830. According to this process, the oil is spread in a thin layer on the heated surface of a conical rotor revolving at high speed. A high vacuum is maintained in the distillation chamber. Under these conditions, there is evaporation, and not boiling, from the hot surface, of the constituents of the unsaponifiable matter whose separation becomes possible in relation to the glycerides, the advantage being that the oil and the unsaponifiable matter, which are reputed to be fragile, are not degraded during the operation.

The invention will be further detailed in the following exemplary embodiments which illustrate the preparation of lupine oil and of wheatgerm oil concentrate, separately or in the form of mixtures, of formulations of compositions based on such mixtures and of indications of their activities.

I. EXAMPLES OF PREPARATION OF A LUPINE OIL AND OF LUPINE OIL UNSAPONIFIABLE MATTER

Example 1: Lupine Oil

Seeds obtained from certified seeds (of *lupinus albus*), marketed by the company CANA, are used.

After a pre-cleaning, the seeds are carefully cleaned (removal of residual foreign particles and seeds, of broken seeds), and can be decorticated.

They are crushed in a roll mill; after hydro-thermal conditioning at a temperature of about 70° C. their moisture varies between 5% and 10%.

The oil is then extracted in an extractor by percolation using hexane. The extractor being filled with ground scales, the extraction is carried out with 4 to 6 washes with hexane for each load.

After each wash, the miscella is pumped to a distiller; after draining, following the last wash, the cake is sent to a solvent-removing device.

The miscella is continuously distilled in a distiller heated by circulation of steam; it is continuously recycled into the distiller.

At the end of the operations, the oil still containing hexane is sent to the final distillation in order to remove the hexane under vacuum (from 10 mm to 35 mm of mercury) between 70° C. and 100° C. by stripping for 10 min.

The composition of a crude oil extracted from seeds according to the above process is indicated below:

Organoleptic characters: oil with an orange-yellow color, having a characteristic odor.

| Fatty acid composition: | |
|---|---|
| myristic acid C14 | $\leq 0.50\%$ |
| palmitic acid C16 | 4 to 10% |
| palmitoleic acid C16' | $\leq 2\%$ |
| stearic acid C18 | $\leq 4\%$ |
| oleic acid C18' | 45 to 65% |
| linoleic acid C18" | 9 to 17% |
| linolenic acid C18'" | 5 to 11% |
| arachidic acid C20 | $\leq 3\%$ |
| gadoleic acid C20' | 2 to 8% |
| behenic acid C22 | $\leq 6\%$ |
| erucic acid C22' | $\leq 5\%$ |
| lignoceric acid C24 | $\leq 2\%$ |
| Content of unsaponifiable matter | $\geq 1.5$ g/100 g |
| Content of carotenes (in mg/100 g) | $\geq 25$ mg/100 |
| Content of tocopherols | $\geq 0.1$ g/100 |
| Content of phenol derivatives (as gallic acid equivalent) | $\geq 20$ ppm |
| Content of triterpenic alcohol (alpha-lupeol) | 0.1 to 1% |
| Content of total sterols: | $\geq 0.8$ g/100 |
| relative % of campesterol | 18 to 24% |
| relative % of stigmasterol | 5 to 10% |
| relative % of β-sitosterol | 48 to 65% |
| relative % of delta-5-avenasterol | <5% |

Example 2: Preparation of a Lupine Oil Concentrate by Molecular Distillation

The molecular distillation is carried out by spreading the oil in a thin layer on the heated surface of a conical rotor rotating at high speed. A high vacuum is maintained in the distillation vessel. Lupine oil as obtained in Example 1 is introduced into an appropriate molecular distillation apparatus which is preferably of the centrifugal type. The supply rate is 10 to 30 kg per hour and preferably between 15 and 20 kg per hour.

The distillation parameters are the following:
temperature: 210° C. to 250° C.;
vacuum of 1 to 10 μm (that is to say 0.13 to 1.3 Pa).

When the percentage distilled is close to 10, this distillate is carefully recovered.

The richness of this distilled fraction in nonsaponifiable material is between 45% and 65%.

The characteristics of the concentrate thus obtained are the following:

| Organoleptic characters: orange-yellow paste | |
| --- | --- |
| Content of squalene | ≈0.2 g/100 g |
| Content of carotenes | ≈22.0 mg/100 g |
| Content of tocopherols | ≈9.0 g/100 g |
| relative % of alpha-tocopherol | ≈1.0% |
| relative % of gamma-tocopherol | ≈80.0% |
| relative % of delta-tocopherol | ≈15.0% |
| Content of total sterols | ≈40.0 g/100 g |
| relative % of campesterol | ≈20.0% |
| relative % of stigmasterol | ≈9.0% |
| relative % of β-sitosterol | ≈60.0% |
| relative % of delta-5-avenasterol | ≈2.0% |
| relative % of delta-7-stigmasterol | ≈2.0% |
| Content of phenol derivatives, expressed as gallic acid | ≈40.0 ppm |
| Content of total unsaponifiable matter | ≈60.0% |

Example 3: Preparation of the Lupine Oil Unsaponifiable Matter

The lupine oil concentrate obtained in Example 2 is saponified in a stainless steel reactor under the following conditions:
  20 kg of potassium hydroxide scales, 250 kg of alcohol and 30 kg of water are added per 100 kg of concentrate.
  The mixture is heated under reflux for 5 hours.

The aqueous-alcoholic solution of soaps which is thus obtained is diluted by its volume with demineralized water and extracted with dichloroethane (DCE) in a countercurrent apparatus, for example a pulsed column, which selectively extracts the unsaponifiable part.

This solution of unsaponifiable matter is then washed with water in another countercurrent apparatus so as to remove the soaps carried over during the extraction.

The DCE is removed in an amount of about 95% under atmospheric pressure in a falling film evaporation apparatus, and then the evaporation is completed in a jacketed apparatus under vacuum provided with an injector allowing the introduction of live steam within the mass, according to the following procedure:
  The product is heated at 100° C., under a vacuum of 10 mm of Hg (that is to say 1.3 kPa) until the distillation of the residual dichloroethane ceases; at this time, the steam is injected within the mass, at the rate of 4% by weight of water relative to the weight of unsaponifiable matter. The duration of the operation is about 4 hours.
  The product is dried by injection of nitrogen, using the tubing which served for the introduction of the steam.
  The product is then cooled and the vacuum is broken under a nitrogen stream.

The unsaponifiable matter is stored in a high-density polyethylene barrel and a low-density polyethylene bag under nitrogen until required.

The lupine oil unsaponifiable matter thus obtained is an orange-yellow paste containing:

tocopherols about 3%
of which about 96% of gamma-tocopherol
and about 4% of alpha-tocopherol

| | |
| --- | --- |
| tocopherols about 3% | |
| of which about 95% of gamma-tocopherol and about 4% of alpha-tocopherol | |
| sterols about 40% with a relative content of: | |
| campesterol about 25% | |
| stigmasterol about 8% | |
| β-sitosterol about 52% | |

Example 4: Mixture of a Wheatgerm Oil Concentrate and Lupine Oil

A wheatgerm oil concentrate is prepared according to the process described in Patent FR 92 07830 whose content is incorporated herein by reference, and it is mixed with lupine oil as obtained in Example 1, in the respective proportions by weight of 30% and 70% relative to the total weight of the mixture. The characteristics of the mixture obtained are the following:

Organoleptic characters: clear oil with an orange-yellow color, having a characteristic odor.

| Fatty acid composition: | |
| --- | --- |
| myristic acid C14 | ≦2% |
| palmitic acid C16 | 7 to 14% |
| palmitoleic acid C16' | ≦2% |
| stearic acid C18 | ≦5% |
| oleic acid C18' | 38 to 52% |
| linoleic acid C18" | 25 to 30% |
| linolenic acid C18'" | 4 to 11% |
| arachidic acid C20 | ≦3% |
| gadoleic acid C20' | 2 to 8% |
| behenic acid C22 | 1 to 6% |
| erucic acid C22' | ≦5% |
| lignoceric acid C24 | ≦2% |
| content of unsaponifiable matter | ≧4 g/100 g |
| content of carotenes (in mg/100 g) | ≧15 mg/100 g |
| content of tocopherols | ≧500 mg/100 g |
| content of phenol derivatives | ≧14 mg/kg |
| content of total sterols: | ≧2.5% |
| relative % of campesterol | 18 to 25% |
| relative % of stigmasterol | 3 to 10% |
| relative % of β-sitosterol | 48 to 64% |
| relative % of delta-5-avenasterol | ≦6% |

II. EXAMPLES OF FORMULATION (THE PRODUCTS DESIGNATED BY TRADE NAMES ARE, UNLESS OTHERWISE STATED, CITED IN THE INCI DIRECTORY; 6TH EDITION

| 1. Lupine oil cream | |
| --- | --- |
| Montanov 68 | 5.00% |
| Shea butter | 3.00% |
| Paraffin oil | 10.00% |
| Cetaryl octanoate | 5.00% |
| Dimethicone | 1.00% |
| Lupine oil | 5.00% |
| Phenoxyethanol | 0.40% |
| Phenonip | 0.80% |
| Water | 59.10% |

1. Lupine oil cream

| | |
|---|---|
| Glycerin | 10.00% |
| Controx VP | 0.10% |
| Perfume borealis No. 1 | 0.60% |

2. Light lupine oil moisturizing cream

| | |
|---|---|
| Thick liquid petrolatum | 2.00% |
| Octyl dodecanol | 2.00% |
| Cetaryl glucoside | 5.00% |
| Jojoba oil | 1.00% |
| Squalane | 1.00% |
| Cetostearyl alcohol 25 EO | 1.00% |
| Controx VP | 0.10% |
| Lupine oil | 5.00% |
| Purified water | 72.475% |
| Trisodium citrate | 0.10% |
| Citric acid monohydrate | 0.025% |
| Silicone Q21401* | 4.00% |
| Preservative GD 700** | 0.20% |
| Sepigel 305 | 0.80% |
| Aloe vera gel | 5.00% |
| Perfume composition 53905-1 Synarome | 0.30% |

*the silicone Q21401 is marketed by the company Dow Corning under the name cyclomethicone and dimethiconol;
**the preservative GD 700 is marketed by the company PHYTOCOS under: propylene glycol, water, phenoxy-ethanol, methylparaben, butylparaben, isobutylparaben, ethylparaben; methylchlorothiazolinone and methyl-isothiazolinone.

3. Lupine oil concentrate cream

| | |
|---|---|
| Polyoxyethylenated fatty acid esters | 4.00% |
| Stearic acid | 3.00% |
| Cetyl alcohol | 2.00% |
| Fluid liquid petrolatum | 2.00% |
| Propylene glycol | 2.00% |
| Glycerin | 1.50% |
| Lupine oil concentrate | 1.00% |
| Polyimidazole urea | 0.20% |
| Methyl parahydroxybenzoate | 0.20% |
| Propyl parahydroxybenzoate | 0.10% |
| Tartaric acid | 0.02% |
| Perfume | 0.30% |
| Water . . . qs | 100.00% |

4. Lupine unsaponifiable matter cream

| | |
|---|---|
| Polyoxyethylenated sorbitan monostearate | 3.20% |
| Octyldodecanol | 3.00% |
| Sweet almond oil | 2.80% |
| Sorbitan monostearate | 2.00% |
| Fluid liquid petrolatum | 2.00% |
| Hexyl laurate | 2.00% |
| Beeswax | 2.00% |
| Cetyl alcohol | 1.50% |
| Diethylene glycol stearate | 1.50% |
| Mixture of monoglycerides of fatty alcohols of triglycerides and waxy esters | 1.00% |
| Lupine unsaponifiable matter | 1.00% |
| Methyl parahydroxybenzoate | 0.30% |
| Propyl parahydroxybenzoate | 0.10% |
| Perfume | 0.25% |
| Water . . . qs | 100.00% |

5. Anti-age cream with a mixture comprising 30% of concentrate of wheatgerm oil and 70% of lupine oil

| | |
|---|---|
| Arlacel 165 | 5.00% |
| Cetaryl octanoate | 14.00% |
| Cetyl palmitate | 1.00% |
| Concentrate of wheatgerm oil and lupine oil | 3.00% |
| Phenonip | 0.80% |
| Phenoxyethanol | 0.40% |
| Controx VP | 0.10% |
| Water | 72.50% |
| Sepigel | 2.50% |
| Perfume Firmenich petit matin | 0.70% |

6. After-sun milk with a mixture comprising 30% of a concentrate of wheatgerm oil and 70% of lupine oil

| | |
|---|---|
| Emulgade SE* | 6.00% |
| Miglyol 812 | 3.00% |
| Cetaryl octanoate | 3.00% |
| Shea butter | 2.00% |
| Cetyl alcohol | 1.00% |
| Concentrate of wheatgerm oil and lupine oil | 1.50% |
| Silicone Q2 1401 | 2.00% |
| Water | 76.90% |
| Glycerin | 3.00% |
| Controx VP | 0.10% |
| Phenonip | 0.80% |
| Phenoxyethanol | 0.40% |
| Perfume sea water TM 4509 Technicoflor | 0.30% |

*Emulgade SE is marketed by the company Henkel under: glyceryl stearate, ceteareth-20, ceteareth-12, cetaryl alchool and cetyl palmitate.

7. Antisun cream with a mixture comprising 30% of a concentrate of wheatgerm oil and 70% of lupine oil

| | |
|---|---|
| Water | qs 100% |
| Caprylic/Capric triglyceride | 16.10% |
| Titanium dioxide | 10.00% |
| Octyl palmitate | 4.64% |
| C12–15 alkyl benzoate | 4.00% |
| Cyclomethicone | 3.00% |
| Cetaryl octanoate | 3.50% |
| Cetyl dimethicone copolyol | 2.50% |
| Zinc oxide | 2.00% |
| Aluminum/magnesium hydroxide stearate | 2.00% |
| Cetyl dimethicone | 1.00% |
| Isostearic acid | 1.00% |
| Sodium chloride | 1.00% |
| Phenoxyethanol | 0.876% |
| Tocopheryl acetate | 0.50% |
| Octyldodecanol | 0.28725% |
| Methylparaben | 0.128% |
| Butylparaben | 0.048% |
| Concentrate of wheatgerm oil and lupine oil | 2.00% |

8. Antisun cream with a mixture comprising 30% of a concentrate of wheatgerm oil and 70% of lupine oil

| | |
|---|---|
| Water | qs 100% |
| Octyl methoxycinnamate | 7.50% |
| Octyl cocoate | 10.00% |
| Octyl salicylate | 5.00% |

-continued

8. Antisun cream with a mixture comprising 30% of a concentrate of wheatgerm oil and 70% of lupine oil

| | |
|---|---|
| Oleth-2 | 3.00% |
| Benzophenone-3 | 3.00% |
| Liquid petrolatum | 1.80% |
| Stearyl heptanoate | 1.425% |
| Stearamine oxide | 1.30% |
| Acrylates/octylacrylamide copolymer | 1.30% |
| Magnesium sulfate | 0.50% |
| Vitamin E | 0.50% |
| Sodium magnesium silicate | 0.40% |
| Phenoxyethanol | 0.053% |
| Methylparaben | 0.012% |
| Perfume | 0.20% |
| Concentrate of wheatgerm oil and of lupine oil | 1.00% |

III. STUDY OF THE ANTI-FREE RADICAL ACTIVITY OF A MIXTURE OF LUPINE OIL AND CONCENTRATE OF WHEATGERM OIL: COMPARISON WITH VITAMIN E AND VITAMIN C COMBINED WITH GLUTATHIONE

1. Products Tested

Five samples having the references below were tested:

L0: wheatgerm oil

L50: mixture of 50% concentrate of wheatgerm oil and 50% lupine oil

L70: mixture of 30% concentrate of wheatgerm oil and 70% lupine oil

L90: mixture of 10% concentrate of wheatgerm oil and 90% lupine oil

L100: pure lupine oil

The activity of these five batches was compared with that of vitamin E acetate (Sigma), of a sodium ascorbate (vitamin C) and glutathione (Sigma) combination, as well as to that of a 30% solution of β-carotene in a synthetic glyceride (Reference 1) and to that of a mixture of 50% by weight of concentrate of wheatgerm oil and 50% by weight of concentrate of sesame oil (as described in Patent FR 92 07830) (Reference 2).

2. Materials and Methods

2.1. Cell Cultures

The cells are human epidermal keratinocytes. Keratinocytes were obtained from surgical waste resulting from plastic surgery on the breast carried out on a 40-year-old woman (donor BIOPREDIC No. VACHL0009). The cells are used at the sixth passage, they are inoculated at $1 \times 10^5$ cells per well into 6-well culture plates. They are used at confluence.

2.2. Evaluation of the Anti-Free Radical Activity

It is quantified by a fluorometric method which detects the quantity of hydroperoxides which are metabolites of free radicals. An appropriate probe which converts to a fluorescent derivative in their presence is used, according to the method described by Keston A. S. and Brandt R. (The fluorometric analysis of ultramicro quantities of hydrogen peroxide, Anal. Biochem. 11, 1965, 1–5).

2.3. Irradiation in the U.S. and Observations of the Effects of Irradiation The free radicals are generated at the cell culture level by irradiation with ultraviolet A rays. The keratinocytes are irradiated with UVA rays on the bottom side of the monolayer (in order to avoid the possible screening effects of the test products) with the aid of an ultraviolet table (VILBERT LOURMAT) for 90 minutes (10 J/cm$^2$)

The test products as well as the two reference products, reference 1 and reference 2, are solubilized in dimethylformamide (DMF).

The test products, L0, L50, L70, L90 and L100 are tested at concentrations of 0.000001; 0.00001; 0.0001; 0.001 and 0.01% (w/v) (that is to say 1; 10; 100; 1000 and 10,000 ppm) in HBSS buffer (Hacks' saline solution) containing 0.04% (v/v) of DMF.

The DMF concentration is kept constant at 0.04% (v/v) in each dilution.

References 1 and 2 are tested at 0.01% (w/v) in the HBSS buffer containing 0.04% (v/v) of DMF.

The vitamin C at 0.5 mg/ml+glutathione at 0.5 mg/ml mixture and the vitamin E acetate at 0.1% (w/v) are directly solubilized in the HBSS buffer.

The probe intended to detect the hydroperoxides (CM-H2DCF-DA probe marketed by MOLECULAR PROBES) was used at 5 $\mu$M in the test medium.

The keratinocytes are incubated at ambient temperatures with the test products and the reference products during the irradiation, that is to say 90 minutes.

2.4. Controls

Control keratinocytes irradiated (+UVA) or not irradiated (−UVA) with UVA rays are incubated in the HBSS buffer (with control (DMF) or without (DMF) at 0.04% (v/v)) and containing only the probe during the duration of the irradiation.

After irradiation, the keratinocytes are lyzed by the action of ultrasound. The cellular lysates are transferred into 96-well plates and analyzed by fluorimetry with the aid of a plate analyzer (excitation: 355 nm, emission: 460 nm).

The results are expressed in fluorescence unit/culture well.

3. Results

The groups of data (control group and treated groups) were compared by a one-way analysis of variance (ANOVA 1), followed by a Dunnett test.

The percentage protection of the test products or of the reference products $R_1$ and $R_2$ was calculated with the aid of the following formula:

$$\% \text{ protection} = \frac{\begin{bmatrix} \text{mean value} \\ \text{obtained with} \\ \text{the irradiated} \\ \text{control} \end{bmatrix} - \begin{bmatrix} \text{mean value} \\ \text{obtained with} \\ \text{the test products} \\ \text{or the reference} \\ \text{products} \end{bmatrix}}{\begin{bmatrix} \text{mean value} \\ \text{obtained with} \\ \text{the irradiated} \\ \text{control} \end{bmatrix} - \begin{bmatrix} \text{mean value} \\ \text{obtained with} \\ \text{the nonirradiated} \\ \text{control} \end{bmatrix}} \times 100$$

By convention, when the values measured in the presence of the test products or in the presence of the reference products were less than those of the "non-irradiated control", the percentage protection was expressed as 100%. Likewise, when these values were greater than those for the "irradiated control", the percentage protection was expressed as 0%.

The tables below (Tables 1 to 7) present the results obtained expressed as % protection.

TABLE 1

|  | Control −UVA | Control +UVA | Vitamin C + glutathione | Vitamin E acetate | Ref. 1 0.01% (w/v) | Ref. 2 0.01% (w/v) |
|---|---|---|---|---|---|---|
| % protection | 100 | 0 | 100 | 65 | 62 | 93 |

TABLE 2

| Control DMF −UVA | Control DMF +UVA | L 0 (% w/v) | | | | |
|---|---|---|---|---|---|---|
| | | 0.000001 | 0.00001 | 0.0001 | 0.001 | 0.01 |
| % protection 100 | 0 | 64 | 56 | 96 | 28 | 23 |

TABLE 3

| Control DMF − UVA | Control DMF− UVA | L 50 (% w/v) | | | | |
|---|---|---|---|---|---|---|
| | | 0.000001 | 0.00001 | 0.0001 | 0.001 | 0.01 |
| % protection 100 | 0 | 38 | 60 | 66 | 17 | 58 |

TABLE 4

| Control DMF − UVA | Control DMF + UVA | L 70 (% w/v) | | | | |
|---|---|---|---|---|---|---|
| | | 0.000001 | 0.00001 | 0.0001 | 0.001 | 0.01 |
| % protection 100 | 0 | 51 | 95 | 86 | 0 | 0 |

TABLE 5

| Control DMF − UVA | Control DMF+ UVA | L 90 (% w/v) | | | | |
|---|---|---|---|---|---|---|
| | | 0.000001 | 0.00001 | 0.0001 | 0.001 | 0.01 |
| % protection 100 | 0 | 8 | 64 | 56 | 60 | 27 |

TABLE 6

| Control DMF − UVA | Control DMF− UVA | L 100 (% w/v) | | | | |
|---|---|---|---|---|---|---|
| | | 0.000001 | 0.00001 | 0.0001 | 0.001 | 0.01 |
| % protection 100 | 0 | 24 | 26 | 33 | 79 | 87 |

The results presented in Tables 1 to 6 make it possible to draw the following conclusions:

DMF at 0.04% (v/v), used as intermediate solvent for the test products and for the reference products (ref. 1 and ref. 2) has no significant effect on the intensity of the fluorescence emitted by the probe, before and after irradiation of the cells.

The two reference products vitamin C+glutathione, on the one hand, and vitamin E acetate on the other exhibit an expected protective effect of 100% and 65% respectively toward the damaging effect of UVA rays.

The reference products, ref. 1 and ref. 2 tested at 0.01% (w/v), have a protective effect of 62% and 93% respectively toward the damaging effect of UVA rays.

As regards the test products, the following results are observed:

a protective effect is obtained with the products L 0, L 50, L 70, L 90 and L 100 toward the damaging effects of UVA-rich UV rays.

product L 0 (100% of wheatgerm oil concentrate) is more protective at the low concentrations tested than at the high concentrations.

an opposite effect is observed for product L 100 (100% lupine oil).

the L 50 and L 90 mixtures are not better than the L 0 and L 100 products.

on the other hand, unexpectedly, product L 70, especially at a concentration of 0.0001% (w/v) is significantly more protective than the other four products.

IV. STUDY OF THE ANTIELASTASE ACTIVITY OF PRODUCT L b 70IN A HUMAN SKIN EXPLANT MODEL

The study of the antielastase activity represents a good indication of skin aging since it is now well known that the degradation of the elastic fibers present in the dermis involves endogenous elastases. The test used makes it possible to study the antielastase activity in vitro in sections of human skin explant. An application of purified elastase on a limited portion of the section is accompanied by degradation of the endogenous elastic fibers. The elastic fibers are stained with (+)-catechin. The percentage of intact elastic fibers per optical field is evaluated by image analysis. A product having antielastase activity makes it possible to preserve the integrity of the elastic fibers in the presence of purified elastase.

1. Products tested

Product L 70, previously tested for its anti-free radical activity, was compared with reference antielastase products: elastinal (Sigma) and mercuric chloride (Sigma).

2. Materials and methods 2.1. Reagents

A pancreatic elastase (type IV, reference E0258, Sigma) is used. The medium for incubation of the human skin sections ("vehicle") is 0.1 M Herpes buffer, adjusted to pH 7.5 with sodium hydroxide containing 0.1 M sodium chloride.

2.2. Test System

The skin sections are produced from surgical waste collected after abdominal plastic surgery. The donor was a 37-year-old woman. Explants of 1 cm in diameter are produced and they are deposited on a cork support and they are frozen at −80° C. Transverse sections 6 pm thick are produced with a cryomicrotome. The sections are fixed on glass slides and maintained hydrated with the vehicle during the test.

2.3. Preparation of the Test Products and of the Reference Products, Incubation with the Test System The test products are tested at 0.5; 1 and 5% (v/v) in the vehicle.

The elastatinal is tested at 0.01 and 0.1% (w/v) in the vehicle.

The mercuric chloride is tested at 0.025 and 0.125% (w/v) in the vehicle.

The dilutions of the test products and of the reference products are deposited on the skin sections in an amount of 100 µl per section (0.32 cm² in surface area), and preincubated for ten minutes at 37° C. Filter paper strips (0.16 cm² in surface area) impregnated with the vehicle alone (control vehicle) or containing pancreatic elastase at 5 international units (IU)/ml (control enzyme) are deposited on the sections. The slides are placed in a humid chamber at 37° C. for three hours.

2.4. Evaluation of the Antielastase Activity

After incubation, the sections are rinsed with the incubation medium and stained with (+)-catechin. The activity of the enzyme in the absence and in the presence of the test products or of the reference products is evaluated by image analysis: the image of the stained sections is digitized on a video screen; a software for image analysis makes it possible to measure the amounts of gray in the binary images; the surface area occupied by the intact elastic fibers is measured. The results are expressed as percentage of intact elastic fibers per optical field.

The percentage inhibition of the elastase activity of the test products and of the reference products is calculated with the aid of the following formula:

$$\% \text{ inhibition} = \frac{\begin{bmatrix}\text{Value obtained}\\ \text{with the control}\\ \text{enzyme}\end{bmatrix} - \begin{bmatrix}\text{Value obtained}\\ \text{with the test}\\ \text{products or the}\\ \text{reference products}\end{bmatrix}}{\begin{bmatrix}\text{Value obtained}\\ \text{with the control}\\ \text{vehicle}\end{bmatrix} - \begin{bmatrix}\text{Value obtained}\\ \text{with the control}\\ \text{enzyme}\end{bmatrix}} \times 100$$

The results are shown in the table below (Table 7).

TABLE 7

| Product | Concentration % (v/v) | % Inhibition |
|---|---|---|
| Control vehicle | — | 100 |
| Control enzyme | — | 0 |
| Mercuric chloride | 0.025(w/v) | 18.4 |
|  | 0.125(w/v) | 39.3 |
| Elastatinal | 0.01 (w/v) | 71.5 |
|  | 0.1 (w/v) | 59.9 |
| L 70 | 0.5 | 31 |
|  | 1 | 70 |
|  | 5 | 70 |

The calculation of the percentage inhibition of the elastase activity unexpectedly gives 100% in the absence of elastase (control vehicle) and 0% in the presence of elastase (control enzyme).

The elastatinal, tested at 0.01 and 0.1% (w/v) inhibits the elastase activity by 71% and 60% respectively. The elastine fibers are for a large part intact in the region of application of the elastase.

The mercuric chloride, tested at 0.025 and 0.125% (v/v), inhibits the degradation of the elastine fibers by elastase by 18% and 39% respectively.

L 70, tested at 0.5; 1 and 5% (v/v) inhibits the degradation of the elastine fibers by elastase by 31%, 70% and 70% respectively.

V. STUDY OF THE ANTIELASTASE ACTIVITY OF A CRUDE LUPINE OIL AS OBTAINED IN EXAMPLE 1 AND OF A LUPINE OIL OBTAINED BY THE DIRECT PRESSING OF LUPINE SEEDS (EXPRESSED LUPINE OIL)

The expressed lupine oil is obtained by cold pressing, with a titan-type press, of the decorticated lupine seeds of the *Lupinus albus* species. The cake is continuously recycled in order to extract the residual oil. After the pressing stage, the oil is stored at room temperature in an appropriate tank for 24 hours.

It is then filtered so as to remove the solid material in suspension, such as fibers or phopholipids.

The characteristics of the expressed lupine oil obtained are the following:

Organoleptic characters: oil with an orange-yellow color, having a characteristic odor.

| Fatty acid composition: | |
|---|---|
| myristic acid C14 | ≦0.50% |
| palmitic acid C16 | 4 to 10% |
| palmitoleic acid C16' | ≦2% |
| stearic acid C18 | ≦4% |
| oleic acid C18' | 45 to 65% |
| linoleic acid C18" | 9 to 17% |
| linolenic acid C18'" | 5 to 11% |
| arachidic acid C20 | ≦3% |
| gadoleic acid C20' | 2 to 8% |
| behenic acid C22 | ≦6% |
| erucic acid C22' | ≦5% |
| lignoceric acid C24 | ≦2% |
| Content of unsaponifiable matter | ≦1.5 g/100 g |
| Content of carotenes (in mg/100 g) | about 25 mg/100 g |
| Content of tocopherols | about 120 mg/100 g |
| Content of phenol derivatives (as gallic acid equivalent) | about 30 ppm |
| Content of triterpenic alcohol (alpha-lupeol) | 0.1 to 1% |
| Content of total sterols: | ≦0.8 g/100 g |
| relative % of campesterol | 18 to 24% |
| relative % of stigmasterol | 5 to 10% |
| relative % of β-sitosterol | 48 to 65% |
| relative % of delta-5-avenasterol | <5% |

The antielastase activity is determined under the conditions indicated in IV above.

The results obtained are collated in the table below.

TABLE 8

| Products | Concentration % (v/v) | Inhibition |
|---|---|---|
| Control vehicle | — | +++ |
| Control enzyme | — | 0 |
| Mercuric chloride | 0.125(w/v) | ++ |
| Elastatinal | 0.1 (w/v) | ++ |
| Crude lupine oil | 0.5 | + |
|  | 1 | ++ |
|  | 5 | ++ |
| Expressed lupine oil | 0.5 | + |
|  | 1 | +++ |
|  | 5 | +++ |

The elastatinal and the mercuric chloride were used as reference product.

As expected, in the absence of elastase (control vehicle), no degradation of the fibroblasts is observed.

As expected, the elastatinal, tested at 0.1% (w/v), and the mercuric chloride, tested at 0.125% (w/v), strongly inhibits the enzymatic activity of the elastase. The antielastase activity of the crude lupine oil and that of the expressed lupine oil increase with the concentration. At a concentration of 5% (v/v), the expressed lupine oil completely inhibits the enzymatic activity of elastase.

VI. Study of the antioxidant activity of a composition based on lupine oil or on its fractions in the Rancimat test.

The antioxidant activity is evaluated by the Rancimat test. This test represents an adaptation of the Swift test so as to be automated on a Rancimat apparatus (a version of the Rancimat test is marketed by the company METROHM, Switzerland).

The table below (Table 9) indicates the Rancimat stability results 98° C., 20 l/h) for compositions according to the invention and, by way of comparison, for other oils of plant origin.

TABLE 9

| SAMPLES ANALYZED | RESULTS |
|---|---|
| Lupine oil | 60.4 h |
| Sunflower oil | about 10 h |
| Corn oil | 18.2 h |
| Sesame oil | 20.7 h |
| Lupin oil concentrate | >75 h |

VIII. STUDY OF THE ANTIOXIDANT ACTIVITY OF LUPINE OIL FRACTIONS BY THE ACCELERATED AGING METHOD

The results are presented in Table 10 below.

TABLE 10

| Products | Concentration in the oil (% weight) | Starting peroxide value (m equi-valent/kg) | Peroxide value after 13 days (m equi-valent/kg) |
|---|---|---|---|
| Denatured vegetable oil | — | 3.4 | 18.5 |
| Concentrate | 2.5 | 6.4 | 10.1 |
| Unsaponifiable matter | 2.3 | 2.8 | 6.7 |

The control used is a denatured vegetable oil from which practically all the unsaponifiable matter has been extracted by molecular distillation. It contains mainly triglycerides which are easily oxidizable substrates.

The lupine oil concentrate is as obtained in Example 2 and the unsaponifiable matter is as obtained in Example 3.

After dissolving in the denatured oil, the antioxidant activity of the fractions is tested by an accelerated aging method. A thin film of oil, 2 to 3 mm in thickness, is exposed to air for 13 days, at 50° C.

The oxidative degradation is evaluated by measuring the peroxide value.

The lower the peroxide value after 13 days of exposure, the more marked the antioxidant effect of the various fractions.

It is observed that the oxidation-resistance of the control is increased in the presence of lupine oil concentrate and even more in the presence of unsaponifiable matter. These results therefore demonstrate the antioxidant activity of these lupine oil fractions.

IX. STUDY OF THE DNA-PROTECTING EFFECT

It has also been observed that the compositions according to the invention had a protective effect on the DNA tested using a system for generating reactive oxygen species which induce the formation of lesions on the DNA. This test made it possible to demonstrate, in particular for the composition based on 30% wheatgerm oil concentrate and 70% lupine oil (L70), a significant inhibition of the damage caused by a reactive oxygen species (ROS), the singlet oxygen $O_2$ generated by illumination of methylene blue, an indicator of the protective effect.

1. Products tested

The products of the invention L70, L100, are compared with refined lupine oil and with a control (β-carotene at 3 mg/100 g).

2. Principle of the test used

The test used is a biological system of detecting damage (3-D test) on DNA captured on a microplate (Analytical Biochemistry, 1995, 232, 37–42). The damage is recognized by the repair enzymes and repaired by purified cellular extracts. The repair of the lesions involves a phase for excision and then resynthesis of the damaged and excised DNA fragment. During the reparative synthesis stage, one or more modified nucleotides (digoxigenylated dUTP or DIG-11-dUTP) are incorporated into the DNA. These nucleotides are then recognized by anti-DIG antibodies coupled to alkaline phosphatase. An alkaline phosphatase substrate (Lumi-Phos 530) is then added and the luminescent signal emitted is measured by a luminometer (Lumax 2, marketed by the company S.F.R.I.). The intensity of the signal obtained depends on the different parameters (extracts, salt concentration, quantity of DNA, reaction time and the like) including that relating to the number of lesions repaired, and therefore of lesions present on the DNA. A dose-response relationship is observed within the limit of 1 to 15 lesions per 6 kilobases for most of the lesions.

This system is capable of repairing any type of lesion since all the enzymes for repairing DNA lesions are present and active in the extracts. The oxidative damage is therefore recognized in this system.

The damage is caused by by reactive oxygen species (ROS) by means of a system which induces the formation of lesions on the DNA adsorbed in a well, leading to the reading of a reparative synthesis signal. In the presence of a compound or of a mixture of compounds which make it possible to protect DNA as a result, for example, of anti-oxidant or anti-free radical properties, a decrease or even an elimination of the repair signal, a reflection of the quantity of lesions, is observed.

ROS $^1O_2$, a powerful electrophile which has a very short life, is generated by illumination of methylene blue. It therefore reacts very rapidly with the bases in the DNA and produces various types of damage such as modification of bases or loss of bases, which are very genotoxic.

3. Materials and Methods

3.1. Materials

The reagents used are described in the article Analytical Biochemistry, 1995, 232, 37–42.

The chemiluminescent signal is detected with the aid of a luminometer Lumax 2 marketed by the company S.F.R.I.

3.2. Methods

3.2.1. Adsorption of the Target DNA in the Microplate Wells

Ultrapurified plasmid DNA (pBS) (predominantly supercoiled form) is placed in contact with the wells sensitized by poly-lysine for 30 minutes at 30° C., with gentle shaking, at a concentration of 1 µg/ml in a volume of 50 µl. Under these conditions, the adsorption of the DNA is quantitative (about 40 ng per well).

A positive control for repair, consisting of a plasmid predamaged by UV-C (called $pBS^{UV}$), is added.

After incubation, the wells are washed twice with a solution of PBS supplemented with 0.1% Tween 20.

3.2.2. General of ROS by Illumination of Methylene Blue

A stock solution of methylene blue at 10 µg/ml is diluted to a concentration of 4 ng/ml in ultrapure water (MilliQ quality from Millipore).

This solution is mixed in an equal volume with various dilutions of the samples, and 50 µl of the mixture (at 2 ng/ml of methylene blue) are added to the wells containing the adsorbed plasmid DNA. The wells are placed on ice and illuminated for 20 minutes with 2 lamps of 100 W, 30 cm apart.

3.2.3. Dilutions of the Samples to be Tested in the Test of Protection of DNA The four samples were tested at 3 dilutions. The results are presented in Table 9.

The dilutions were made 2X, in propylene glycol, in order to obtain the desired dilutions after addition of a volume of methylene blue solution of 4 ng/ml.

In order to check that the decrease in the repair signal is not aspecific, the same dilutions (IX) are incubated under the same conditions on $pBS^{UV}$. A dilution will exhibit a protective effect only if a decrease in the repair signal is noted, at this dilution, in the presence of methylene blue, and an absence of modification of the signal on $pBS^{UV}$. An inhibition of the control repair signal for $pBS^{UV}$ can, for example, be explained by a direct interaction of the sample with the DNA which blocks access of the lesions to the repair enzymes.

These different dilutions were incubated on the nondamaged DNA (pBS) and illuminated in the absence of methylene blue. This test makes it possible to check that the product tested is not genotoxic.

TABLE 11

| Compound tested | Dilution or concentration | % Specific inhibition | % Aspecific inhibition |
|---|---|---|---|
| L 70 (%) | 0.01 | 19 | 3 |
|  | 0.1 | 96 | 6 |
|  | 1 | 92 | 28 |
| L100 (%) | 0.01 | 58 | 4 |
|  | 0.1 | 54 | 6 |
|  | 1 | 69 | 52 |
| Refined lupine oil (%) | 0.01 | 56 | 27 |
|  | 0.1 | 45 | 43 |
|  | 1 | 62 | 24 |
| Control (%) | 0.01 | 45 | 0 |
|  | 0.1 | 53 | (+2) |
|  | 1 | 45 | 0 |
| Propylene glycol (%) | 0.01 | 0 | 2 |
|  | 0.1 | 6 | 6 |
|  | 1 | 13 | 7 |

4. Results

They are expressed as the percentage residual repair inhibition. The 0% value corresponds to the repair signal under the condition of methylene blue treatment alone.

Likewise, an inhibition of the repair signal can sometimes be observed in an aspecific manner (in the absence of ROS), it being possible for this to be due to a direct interaction of the compound with the DNA (desorption of the DNA from the well, aspecific combination with the DNA which will mask the lesions from the repair enzymes and the like). A control consisting in incubating the agents tested with pre-lesioned DNA is therefore added. A decrease in the signal under this condition reflects an aspecific inhibition of the compound, independent of its possible properties of protection of DNA against oxidative damage.

The values given in Table 11 are calculated from the values in RLU, as follows:

The percentage of specific inhibition is calculated as the relative decrease in the lesion effect due to the singlet oxygens generated by the illuminated methylene blue (MB), that is to say $$\frac{[RLU\ MB] - [RLU\ MB + \text{dilution test}]}{[RLU\ MB]} \times 100$$

RLU: Relative Light Unit;

MB: Condition methylene blue+light

The greater a compound's inhibition of the damage caused by singlet oxygen, the greater its protective effect, but it is necessary to take into account, for the interpretation of these results, the aspecificity of the inhibition of the signal.

The propylene glycol used as internal standard exhibits only very weak protective properties on its own, which are not very significant, with respect to singlet oxygen. Its effect is therefore negligible and it therefore constitutes the negative control.

The compound L70 thus exhibits definite protective properties towards singlet oxygen. Its aspecific effect is low.

The efficacy of the compound L100 is also satisfactory.

As regards the refined lupine oil, a high aspecificity at the three doses tested does not make it possible to conclude as to its efficacy with certainty.

The control does not exhibit a dose-effect, but does not show, on the other hand, aspecificity.

Finally, none of the products tested appears to be genotoxic because no increase in the repair signal was observed following incubation of the products on DNA.

What is claimed is:

1. A composition comprising lupine oil or one or more of its fractions for use as an antioxidant and/or antielastase.

2. The composition of claim 1, wherein said lupine oil is obtained from lupine meal and/or seeds.

3. The composition of claim 1, wherein said lupine oil is obtained from a sweet lupine variety.

4. The composition of claim 3, wherein said lupine oil is obtained from *lupinus albus*.

5. The composition of claim 1, wherein said fraction is a lupine oil concentrate, obtained by molecular distillation of said oil.

6. The composition of claim 5, wherein said fraction is an unsaponifiable fraction contained in a concentrate obtained by molecular distillation of said oil.

7. The composition of claim 6 wherein the quantity by weight of the unsaponifiable fraction in the lupine oil concentrate is about 30 % to about 70 %.

8. The composition of claim 1, which contains a lupine oil fraction comprising phenol derivatives.

9. A composition comprising polyphenol derivatives extracted from lupine oil for use as an antioxidant and/or antielastase.

10. The composition of claim 9, comprising at least 20 ppm of said phenol derivatives.

11. The composition of claim 1, comprising wheat germ oil or one or more fractions thereof.

12. The composition of claim 11, wherein said wheat germ oil fraction is a concentrate obtained by molecular distillation of said oil.

13. The composition of claim 12, wherein said wheat germ oil fraction is an unsaponifiable fraction contained in a concentrate obtained by molecular distillation of said oil.

14. The composition of claim 12, wherein said composition contains a wheat germ oil concentrate in the form of a mixture with lupine oil.

15. The composition of claim 14, wherein the amount by weight of concentrate of wheat germ oil and of lupine oil vary respectively between about 10% and about 90% and between about 90% and about 10% so that the amount of said wheat germ oil and lupine oil is 100% in total.

16. The composition of claim 15, wherein the quantities by weight of concentrate of wheat germ oil and of lupine oil are respectively 30% and 70%.

17. The composition of claim 1 wherein said use is selected from the group consisting of a cosmetic composition, an antioxidant, an anti-free radical agent, an antielastase agent, an agent for protecting against UVA and/or UVB, and an agent for protecting DNA against damage.

18. The composition of claim 1 which is a pharmaceutical further comprising a dermatological carrier.

19. The composition of claim 18 wherein said pharmaceutical prevents or treats the effects of UVA and/or UVB radiation on the skin at the epidermal, dermal, cellular or extracellular levels.

20. The composition of claim 18, wherein said pharmaceutical prevents or treats the effects of oxidation, of elastase and of free radicals on the skin.

21. The composition of claim 18, wherein said pharmaceutical is an agent having an activity of protecting DNA against damage.

22. The composition of claim 1 further comprising a physiologically acceptable vehicle.

23. The composition of claim 22, wherein said use is selected from the group consisting of use as an antisun product for protecting against UVB and/or A radiation and/or infrared radiation, a restructuring or toning cream, a cream, for the prevention and the regression of vibices, a nutritive cream, an antiwrinkle cream, a cream for combating aging of the skin, epidermis and dermis, a protective day cream, a contour cream for the lips and the eyes, and regenerative and protective lipsticks.

24. The composition of claim 23, which is formulated for topical use.

25. The composition of claim 24 wherein the total content by weight of lupine oil or the fractions thereof and wheat germ oil or fractions thereof of said composition is of the order of about 0.5% to about 10%.

26. Method of improving the appearance of an individual comprising administering on the skin surface of an individual the composition of claim 1.

27. The composition of claim 1 which is a dietary supplement.

28. The composition of claim 6, wherein the quantity by weight of the unsaponifiable fraction in the lupine oil concentrate is about 45% to about 65%.

29. The composition of claim 11, wherein said use is selected from the group consisting of a cosmetic composition an antioxidant, an anti-free radical agent, an antielastase agent, an agent for protecting against UVA and/or UVB, and an agent for protecting DNA against damage.

* * * * *

UNITED STATES PATENT AND TRADEMARK OFFICE
CERTIFICATE OF CORRECTION

PATENT NO. : 6,146,616
DATED : November 14, 2000
INVENTOR(S) : Msika et al.

Page 1 of 1

It is certified that error appears in the above-identified patent and that said Letters Patent is hereby corrected as shown below:

Title page,
Item [73], Assignee, delete "Laboratories Pharmascience" and replace with -- Laboratoires Pharamscience --.

Column 4,
Lines 35 and 37, delete border between lines.

Column 5,
Lines 11 and 14, delete border between lines

Column 6,
Line 14, delete border between lines.
Lines 29 and 30, delete border between lines.

Column 12,
Line 25, delete the title "I.V. STUDY OF THE ANTIELASTASE ACTIVITY OF PRODUCT L b 7OIN A HUMAN SKIN EXPLANT MODEL" replace with -- I.V. STUDY OF THE ANTIELASTASE ACTIVITY OF PRODUCT L 70 IN A HUMAN SKIN EXPLANT MODEL --.

Column 14,
Lines 20 and 22, delete border between lines.

Signed and Sealed this

Fourth Day of December, 2001

Attest:

*Nicholas P. Godici*

NICHOLAS P. GODICI
*Acting Director of the United States Patent and Trademark Office*

*Attesting Officer*